US00PP21040P2

(12) United States Plant Patent
Dümmen

(10) Patent No.: US PP21,040 P2
(45) Date of Patent: Jun. 1, 2010

(54) ***PELARGONIUM* PLANT NAMED 'DUEPAREST'**

(50) Latin Name: *Pelargonium peltatum*
Varietal Denomination: Dueparest

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/319,338

(22) Filed: Jan. 6, 2009

(51) Int. Cl.
*A01H 5/00* (2006.01)

(52) U.S. Cl. ..... Plt./332

(58) Field of Classification Search ..... Plt./332, Plt./324

See application file for complete search history.

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of Ivy *Geranium* plant named 'Dueparest', characterized by its upright to outwardly spreading plant habit; freely basal branching habit; freely flowering habit; red and pink bi-colored double flowers; and good garden performance.

1 Drawing Sheet

Botanical designation: *Pelargonium peltatum.*
Cultivar denomination: 'DUEPAREST'.

BACKGROUND OF THE INVENTION

The present invention relates to a new and distinct cultivar of Ivy *Geranium* plant, botanically known as *Pelargonium peltatum*, and hereinafter referred to by the name 'Dueparest'.

The new Ivy *Geranium* plant is a naturally-occurring whole plant mutation of a proprietary selection of *Pelargonium peltatum* identified as code number E-16-18, not patented. The new Ivy *Geranium* plant was discovered and selected by the Inventor as a single flowering plant from within a population of plants of the parent selection in a controlled greenhouse environment in Rheinberg, Germany in May, 2007.

Asexual reproduction of the new Ivy *Geranium* plant by vegetative terminal cuttings in a controlled greenhouse environment in Rheinberg, Germany since May, 2007, has shown that the unique features of this new Ivy *Geranium* plant are stable and reproduced true to type in successive generations.

SUMMARY OF THE INVENTION

Plants of the new Ivy *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Dueparest'. These characteristics in combination distinguish 'Dueparest 'as a new and distinct cultivar of Ivy *Geranium:*

1. Upright to outwardly spreading plant habit.
2. Freely basal branching habit.
3. Freely flowering habit.
4. Red and pink bi-colored double flowers.
5. Good garden performance.

Plants of the new Ivy *Geranium* differ primarily from plants of the parent selection in flower color as plants of the parent selection have solid red-colored flowers.

Plants of the new Ivy *Geranium* can be compared to plants of *Pelargonium peltatum* 'Duepared', disclosed in U.S. Plant Pat. No. 19,236. In side-by-side comparisons conducted in Rheinberg, Germany, plants of the new Ivy *Geranium* differed primarily from plants of 'Duepared' in plant size as plants of the new Ivy *Geranium* were broader than plants of 'Duepared'. In addition, plants of the new Ivy *Geranium* and 'Duepared' differed in flower color as plants of 'Duepared' had red-colored flowers.

BRIEF DESCRIPTION OF THE PHOTOGRAPH

The accompanying colored photograph illustrates the overall appearance of the new Ivy *Geranium* plant, showing the colors as true as it is reasonably possible to obtain in colored reproductions of this type. Colors in the photograph may differ slightly from the color values cited in the detailed botanical description which accurately describe the colors of the new Ivy *Geranium* plant.

The photograph comprises a side perspective view of a typical flowering plant of 'Dueparest' grown in a 10.5-cm container.

DETAILED BOTANICAL DESCRIPTION

The aforementioned photograph and following observations and measurements describe plants grown in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time three weeks after planting. Plants had been growing for two months when the photograph and the description were taken. In the detailed description, color references are made to The Royal Horticultural Society Colour Chart, 1995 Edition, except where general terms of ordinary dictionary significance are used.

Botanical classification: *Pelargonium peltatum* 'Dueparest'.

Parentage: Naturally-occurring whole plant mutation of a proprietary selection of *Pelargonium peltatum* identified as code number E-16-18, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Upright to outwardly spreading plant habit; uniformly rounded; densely foliated.

*Growth and branching habit.*—Moderately vigorous growth habit; freely basal branching habit with about three basal branches developing per plant.

*Plant height.*—About 18 cm.

*Plant width.*—About 19 cm.

*Lateral branches.*—Length: About 16 cm. Diameter: About 2 mm. Internode length: About 3.3 cm. Texture: Slightly pubescent. Strength: Strong. Color: Close to 144A.

Foliage description:

*Arrangement.*—Alternate; simple.

*Length.*—About 6.6 cm.

*Width.*—About 6.9 cm.

*Shape.*—Reniform.

*Apex.*—Acute.

*Base.*—Peltate.

*Margin.*—Crenate.

*Venation pattern.*—Palmate.

*Texture, upper and lower surfaces.*—Pubescent.

*Color.*—Developing and fully expanded leaves, upper surface: Close to 137A; venation, close to 144A. Developing and fully expanded leaves, lower surface: Close to 144A; venation, close to 144A. Zonation pattern: Not observed.

*Petiole.*—Length: About 5.6 cm. Diameter: About 2.4 mm. Texture, upper and lower surfaces: Smooth, glabrous. Color, upper and lower surfaces: Close to 144A.

Flower description:

*Flower arrangement.*—Double rotate flowers arranged in rounded hemispherical umbels arising from apical leaf axils. Umbels displayed above the foliage on moderately strong peduncles. Flowers face upright to outward.

*Fragrance.*—Not detected.

*Quantity of flowers.*—Freely flowering habit; about 14 flowers per umbel.

*Flowering season.*—Year-round under greenhouse conditions. In outdoor nurseries and gardens in Germany flowering is continuous from spring throughout the summer.

*Flower longevity.*—Individual flowers last about five to seven days on the plant; flowers persistent.

*Umbel height.*—About 5 cm.

*Umbel diameter.*—About 9 cm.

*Flower diameter.*—About 4.5 cm.

*Flower depth (height).*—About 1.5 cm.

*Flower buds.*—Length: About 1.7 cm. Diameter: About 7 mm. Shape: Ovoid. Color: Close to 46B and 56B.

*Petals.*—Quantity per flower: About five or six. Length: About 2.5 cm. Width: About 1.4 cm. Shape: Obovate. Apex: Rounded. Base: Attenuate. Margin: Sinuate. Aspect: Mostly flat. Texture, upper and lower surfaces: Smooth, glabrous. Color: When opening and fully opened, upper surface: Center, close to 55B; towards the margins, close to 46B; venation, close to 46B; color towards the margins becoming closer to 46C with development. When opening and fully opened, lower surface: Center, close to 56B; towards the margins, close to 46B; venation, close to 46B.

*Petaloids.*—Quantity per flower: About five to six. Length: About 2.2 cm. Width: About 1 cm. Shape: Obovate. Apex: Rounded. Base: Attenuate. Margin: Sinuate. Texture, upper and lower surfaces: Smooth, glabrous. Color: When opening and fully opened, upper surface: Center, close to 55B; towards the margins, close to 46B; venation, close to 46B; color towards the margins becoming closer to 46C with development. When opening and fully opened, lower surface: Center, close to 56B; towards the margins, close to 46B; venation, close to 46B.

*Sepals.*—Quantity per flower: Five, arranged in a single whorl. Length: About 1.2 cm. Width: About 5 mm. Shape: Lanceolate. Apex: Apiculate. Base: Attenuate. Margin: Entire. Color, upper and lower surfaces: Close to 144A.

*Peduncle (umbel stem).*—Length: About 9.7 cm. Diameter: About 2 mm to 4 mm. Strength: Moderately strong. Texture: Smooth, glabrous. Color: Close to 144A.

*Pedicel (individual flower stem).*—Length: About 2.3 cm. Diameter: About 1 mm to 2 mm. Strength: Moderately strong. Texture: Pubescent. Color: Close to 144A.

*Reproductive organs.*—Androecium: Stamen quantity per flower: About six. Anther length: About 2 mm. Anther shape: Oval. Anther color: Close to 60A. Pollen amount: Moderate. Pollen color: Close to 28A. Gynoecium: Pistil quantity per flower: One. Pistil length: About 1.1 cm. Stigma shape: Parted. Stigma color: Close to 59A. Style length: About 2 mm. Style color: Close to 2D.

*Seed/fruit.*—Seed and fruit development have not been observed.

Disease/pest resistance: Plants of the new Ivy *Geranium* have not been observed to be resistant to pathogens and pests common to Ivy *Geraniums.*

Garden performance: Plants of the new Ivy *Geranium* have been observed to tolerate rain, wind, and temperatures ranging from about 5° C. to about 40° C. and have demonstrated good garden performance.

It is claimed:

1. A new and distinct Ivy *Geranium* plant named 'Duepar-est' as illustrated and described.

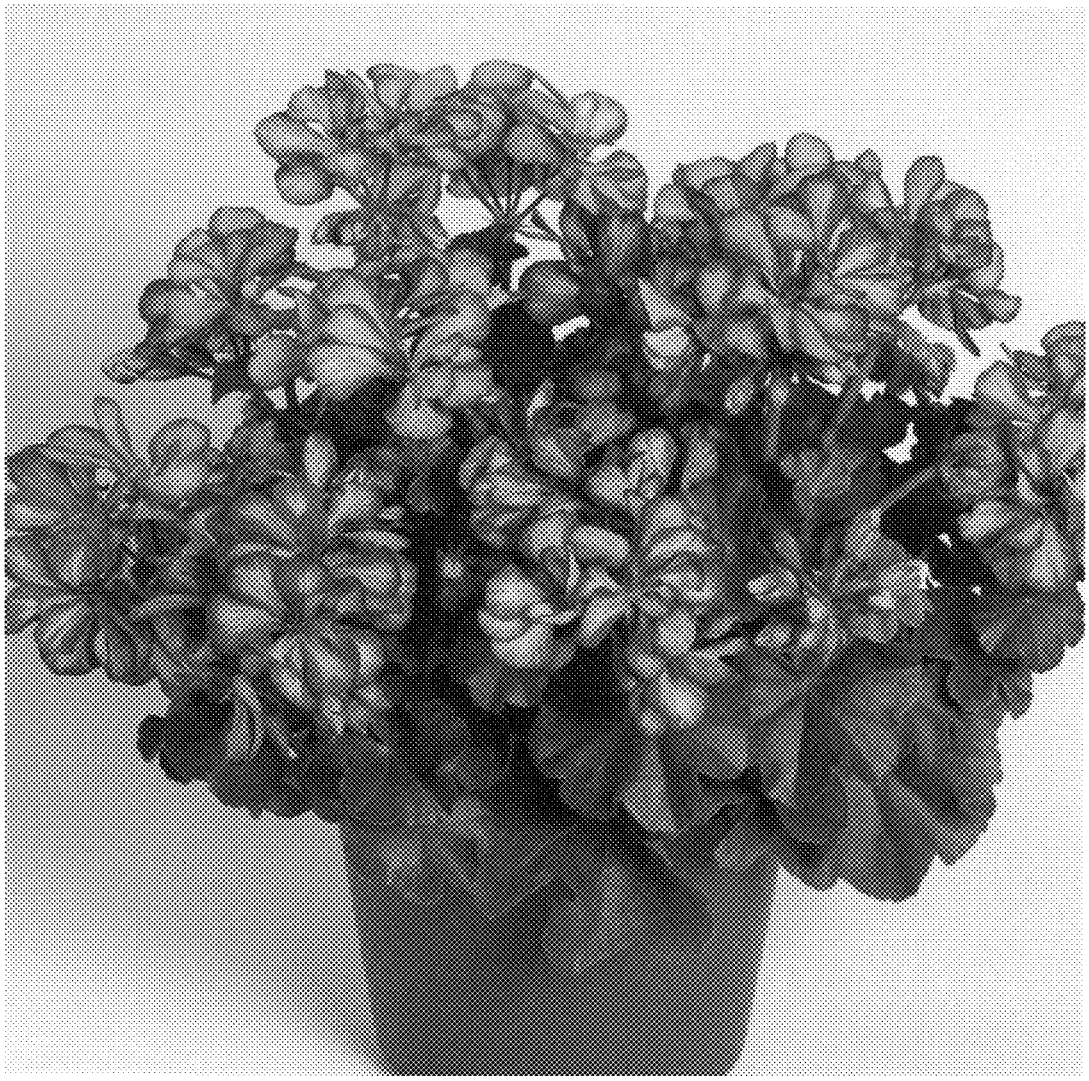

* * * * *